(12) United States Patent
Engstad et al.

(10) Patent No.: US 8,501,710 B2
(45) Date of Patent: Aug. 6, 2013

(54) METHODS OF SKIN TREATMENT AND USE OF WATER-SOLUBLE β-(1,3) GLUCANS AS ACTIVE AGENTS FOR PRODUCING THERAPEUTIC SKIN TREATMENT AGENTS

(75) Inventors: Rolf Engstad, Tromso (NO); Rolf Seljelid, Tromso (NO)

(73) Assignee: Biotec Pharmacon ASA, Tromso (NO)

( * ) Notice: Subject to any disclaimer, the term of this patent is extended or adjusted under 35 U.S.C. 154(b) by 0 days.

(21) Appl. No.: 10/849,417

(22) Filed: May 19, 2004

(65) Prior Publication Data

US 2005/0009781 A1 Jan. 13, 2005

Related U.S. Application Data

(63) Continuation-in-part of application No. 09/936,748, filed as application No. PCT/EP00/01830 on Mar. 3, 2000, now Pat. No. 6,875,754.

(30) Foreign Application Priority Data

Mar. 12, 1999 (DE) .................................. 199 11 054

(51) Int. Cl.
*A61K 31/716* (2006.01)
*A61K 31/715* (2006.01)
(52) U.S. Cl.
USPC ................ 514/54; 514/23; 514/925; 536/4.1; 536/123.1; 536/123.12

(58) Field of Classification Search
USPC ........... 514/54, 23, 887, 836; 536/4.1, 123.1, 536/123.12
See application file for complete search history.

(56) References Cited

U.S. PATENT DOCUMENTS 5,871,751 A * 2/1999 Christensen et al. ...... 424/234.1

FOREIGN PATENT DOCUMENTS

| WO | WO 95/30022 | * 11/1995 |
| WO | WO 96/25951 | * 8/1996 |
| WO | WO 96/28476 | * 9/1996 |

OTHER PUBLICATIONS

Nakamura et al. (Bulletin of Koshien University. A, Vol.; No. 26(A); p. 19-24 (1998) (Abstract sent).*
Nakamura, Hisao, et al., "Beta-1→3)-Glucan Contents of Oats and Protective Effects of Oats Samples on Gastric Stress Ulcer Induced by Water Immersion in Rats," A Bulletin of Koshien University, 26(A): 19-24 (1998).

* cited by examiner

*Primary Examiner* — Shaojia Anna Jiang
*Assistant Examiner* — Michael C Henry
(74) *Attorney, Agent, or Firm* — Rothwell, Figg, Ernst & Manbeck

(57) ABSTRACT

A method of treating an ulcer comprising applying to the ulcer a preparation comprising a water-soluble β-(1,3) glucan with β-(1,6) linked side-chains, where the side-chains comprise β-(1,3) linkages or up to four consecutive β-(1,6) linkages as active ingredients.

10 Claims, 1 Drawing Sheet

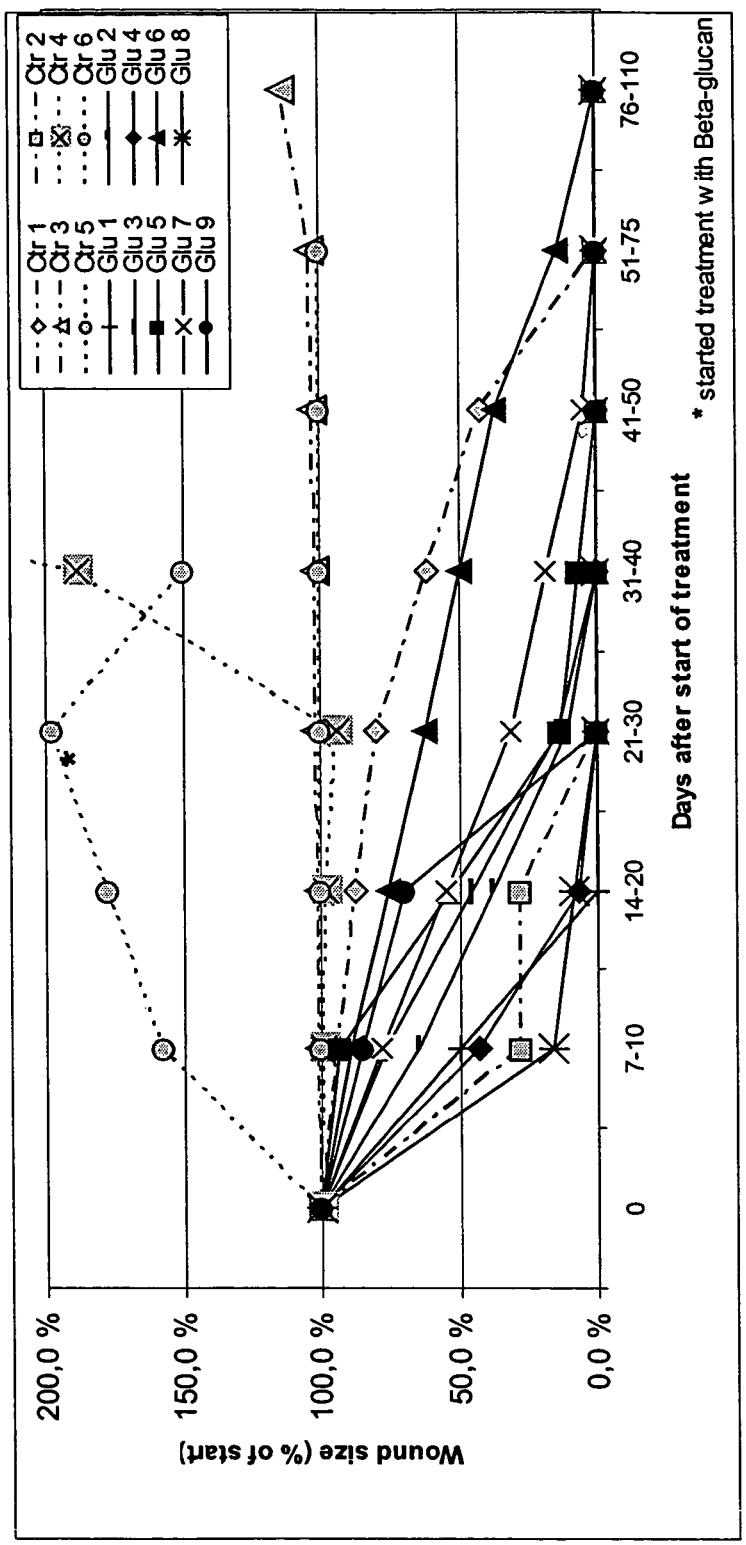

US 8,501,710 B2

METHODS OF SKIN TREATMENT AND USE OF WATER-SOLUBLE β-(1,3) GLUCANS AS ACTIVE AGENTS FOR PRODUCING THERAPEUTIC SKIN TREATMENT AGENTS

REFERENCE

The present application is a continuation-in-part of U.S. application Ser. No. 09/936,748, filed on Sep. 12, 2001, which is incorporated by reference.

BACKGROUND OF THE INVENTION

1. Field of the Invention

The invention relates to the use of specific water soluble β-(1,3) glucans as active agents for combating the formation of wrinkles in the skin as well as epithelial tissue diseases.

2. Description of the Prior Art

The formation of wrinkles caused by increasing age is induced through the degradation of different macro molecules such as for example elastin and collagen, which are responsible for the elastases. Many inflammatory skin diseases, such as for example psoriasis or UV erythema, can also be causatively be linked to an increased concentration of serine proteases, such as e.g. elastase in the upper skin areas (see R. Voegeli et al 1996. in *Cosm. Toil.* 111, 51).

The formation of wrinkles in the skin is normally not counteracted by means of physiological active principles, but by means of cosmetic agents. Many so-called "anti-aging products" contain liposomes loaded with water or aqueous active agents, which through the fat layer of the skin are reaching the epidermis, where they gradually dissolve and through continuous water release compensate the skin recesses and regulate the moisture content of the skin. However, this effect is no combat against the causes, but only has a so-called "repairing effect", which only lasts for a short period of time.

In contrast to this pure cosmetic use, cytostatic active agents are e.g. used for the abatement of psoriasis, such as selenium sulfide, cadmium sulfide, zinc pyrithion or corticosteroid, the medical effect of which resides e.g. in a reduction of the mitose activity in the basal membrane. However, because of the known side effects these substances should not be used over extended periods of time. Further it is possible to alleviate, but not heal, psoriasis by means of antiseptic active agents, such as for example selenium oxide, salicylic acid, pyrithione derivatives, hexachlorophene or quaternary ammonium compounds or by means of cell dissolving and fat removing active substances such as for example benzoy peroxide or tar extracts.

Ulcers manifest as lesions or sores in the skin or mucous membranes resulting from a successive disintegration of surface epithelial tissues that make them distinctive from wounds. The ulcer might be superficial, but in most cases the ulcer extends into deeper layers forming a crater surrounded by defined edges, and is typically very painful. The etiologies of the different ulcers are different, where faulty blood circulation, infection, nerve damage, trauma or cancers might be inductive. Examples of ulcers are diabetic ulcers, plantar ulcers, peptic ulcers, decubitus ulcers, venous ulcers, ischemic ulcers, cancerous ulcers, aphthous ulcers, sublingual ulcers, and atonic ulcers. Whereas, diabetic ulcers are known to have a very complicated etiology, many of the other ulcers have single or defined causes, wherein infections, faulty blood circulation and cancer would be directly involved in the formation of apthous, decubitus, and cancerous ulcers, respectively. An ulcer is considered chronic when it does not heal in a timely fashion.

Diabetic ulcers represent a serious problem because of their delayed or deficient healing often leading to chronic wounds that become high risk for major complications including infections and amputations. The latter is substantiated by the fact that diabetic patients have the highest amputation rate of any type of chronic wound, in some prospective studies as much as 20% of the patients, adding to another 20% experiencing failed healing (see Margolis et al 1999, Diabetes Care 22:692-695). Whereas, the etiology of most wounds and ulcers is identified, that supports the development of preventive care and wound treatment methods and drugs, this is not the case with diabetic ulcers where numerous factors contributing to the chronic wound development are involved. This includes predisposition for atherosclerosis and neuropathy, renal failure, microvascular disease, oedema, preponderance for infections, impaired leukocyte function, increased destruction of growth factors due to increased amounts of matrix metalloproteinases in the wound fluid, and hyperglycemia. In addition, it has been demonstrated that a macrophage dysfunction contributes to the disturbed wound healing process in diabetic ulcers (see Zykova et al. 2000, Diabetes 49:1451-1458). Several approaches to enhance the wound healing process in diabetic ulcers have been employed including the use of transplants and growth factors, but so far with scarcely any success (see Greenhalgh 2003, Clin Plast Surg 30: 37-45).

The use of specific polysaccharides as agents against the skin aging is also known from prior art. It has for example been proposed in U.S. Pat. No. 5,223,491 to use a carboxymethylated β-1,3 glucan, which has been extracted from the yeast fungi *Saccharomyces cerevisiae*, for topical use. However, the glucan is insoluble in water and can therefore only be formulated with large difficulties.

In the European patent application EP-A1 0463540 (Taito) the use of glucans against viruses is described. According to the teachings in the two papers DE-A1 3744345 (Lomapharm) and EP-B1 0175667 (Larm) glucans are only suited for stimulation of the activity of macrophages. The pharmaceutical effect of different glucans is further known from the two European patent applications EP-A1 045338 (Debat) and EP-A1 0561408 (Kaken). The object of the European patent EP-B1 0500718 (Donzis) is the use of water insoluble β-(1,3) glucans, which have been obtained from the cell walls of yeasts, for revitalisation of the skin.

Also known from the prior art are very different solutions known for smoothing of the skin and strengthening of the barrier function from a cosmetic or medical view, which only solve a part of the problem and which may have strong side effects. Especially reference is made to the international patent application WO 98/40082 (Henkel), wherein the use of water soluble β-(1,3) glucans as active agents for the skin treatment is described. These glucans, which preferably are schizopyhallan or krestin, i.e. extracts of fungi, have in practice not shown to be sufficiently effective. The complex task of the invention was therefore to provide active agents which could be used against formation of wrinkles in the skin (cosmetic effect) as well as skin diseases such as, for example, cradle cap, psoriasis, seborrheic dermatitis, seborrhea sicca, seborrhea oleosa, psoriasis vulgaris, ichtyoses, UV erythemas, or ulcers as exemplified by diabetes ulcer and aptheous ulcer (medical effect), and which can be both dermatological and toxicological tolerated and which improve the prior art, as described in WO 94/40082

SUMMARY OF THE INVENTION

A method for treating skin with a specific type of branched water soluble beta-1,3-glucan is described. A defined water soluble beta-glucan is used to promote healing in ulcers as exemplified by diabetic and aphthous ulcers. The soluble beta-glucan can be applied to the affected epithelial layer area directly and when appropriate covered by a gauze pad, or it can be used in various pharmaceutical formulations like rinses, mixtures, gels, ointments, creams, or in combination with other appliances or agents.

DESCRIPTION OF THE FIGURE

FIG. 1: Individual curves for control (broken) and soluble beta-glucan (continuous) patients displayed as percentages of the ulcer areas relative to areas at onset of study. The six patients in the control group are denoted Ctr 1-6, while the nine patients receiving experimental treatment with beta-glucan are denoted Glu 1-9.

DETAILED DESCRIPTION OF THE INVENTION

The object of the invention is the use of water soluble β-(1,3) glucans, which are substantially free from (1,6) linkages, as active agents for preparation of therapeutical agents for skin treatment and skin vitalization, especially for manufacturing of agents which at the same time work against skin aging and formation of wrinkles erythemas and which at the same time stimulate the growth of cells.

It was surprisingly found that water soluble β-glucans, which practically do not have (1,6) linkages, in the Langerhans cells in the deeper skin layers initiate an immuno modulation, whereby the special cytokines are produced and which are significantly superior to the known glucans of the prior art (according to WO 98/40082), which have a significant amount of (1,6) linkages.

Furthermore, it was surprisingly found that water soluble β-glucan applied onto diabetic ulcers gave significant healing efficacy as compared to best conventional wound care. Patients treated with soluble beta-glucan experienced complete healing of the diabetic ulcers during a period of 6 months, whereas only 30% of those receiving conventional wound care experienced healing of the ulcers. Likewise it was surprisingly found that the water soluble beta-glucan gave significant healing efficacy to aphthous ulcers, a condition in which very limited adequate treatments exist.

Water Soluble β-(1,3) Glucans

The term glucans is intended to mean homopolysaccharides based on glucose. Depending on steric linking there is a difference between β-(1,3), β-(1,4) and β-(1,6) glucans. β-(1,3) Glucans normally show a helical structure, whereas glucans with a (1,4) linkage generally have a linear structure. The β-glucans of the invention have a (1,3) structure, i.e. they are substantially free from undesired (1,6) linkages. Preferably, such β-(1,3) glucans are used where the side chains exclusively show (1,3) linkages. Especially the agents contain glucans which are obtained on the basis of yeast from the family *Sacchaomyces*, preferably, *Saccharomyces cerevisiae*. Glucans of this type are utilized in the present invention and are available in technical amounts according to known methods. The international patent application WO 95/30022 (Biotec-Mackzymal) describes e.g. a method for producing such substances, wherein glucans with β-(1,3) and β-(1,6) linkages are brought in contact with β-(1,6) glucanases in such a way, that practically all β-(1,6) linkages are cleaved. More specifically, WO 95/30022 states that the disclosed method ensures that most chains of more than four β-(1,6)-bound glucose units are cleaved off. Moreover, the enzyme treatment will only cleave β-(1,6)-linkages within β-(1,6)-linked chains, but will not remove the β-(1,6)-linked glucosyl residue extending from the branching points. The resulting enzyme treated glucan can be characterized as a branched β-(1,3)-glucan with β-(1,3)-linked sidechains being attached by a β-(1,6)-linkage and being essentially free of β-(1,6)-linked chains. The cleavage allows for up to four consecutive β-(1,6) linkages or zero—four consecutive β(1,6) linkages. Preferably used for the manufacture of these glucans are glucanases based on *Trichoderma harzianum*.

As to the manufacture and availability of the glucans contained in these agents, reference is made to the above-cited publication.

Commercial Applicability

For the purpose of the invention the water soluble β-(1,3) glucans find use as active agents for manufacturing cosmetic and/or pharmaceutical preparations. Typical examples of such agents are skin care agents such as for example anti-wrinkling cremes, anti-cellulitis cremes or sun protection lotions as well as ointments for treating skin diseases such as for example cradle cap, psoriasis, seborrheic dermatitis, seborrhea sicca, seborrhea oleosa, psoriasis vulgaris, ichtyoses, UV erythemas or diabetes ulcers. Normally the water soluble β-glucans can be used in amounts of 0.1 to 25, preferably 0.5 to 15 and especially 1 to 5% by weight, based on the agents. The agents can further as additional auxiliary and additional agents contain mild surfactants, oil bodies, emulsifiers, hyperfatting agents, pearl lustre waxes, consistency substances, thickening agents, polymers, silicon compounds, fats, waxes, stabilizing agents, biogenic active substances, deodorants, agents against dandruff, film forming agents, swelling agents, UV light protection factors, antioxidants, inorganic colour pigments, hydrotropes, preservatives, insect repellents, self tanning agents, solubilizing agents, perfume oils, colouring agents and the like.

The water soluble beta-glucan is used to promote the healing of chronic ulcers, and various types of ulcers caused by poor blood circulation, infection, nerve damage, trauma or cancer, for example, diabetic ulcers, plantar ulcers, peptic ulcers, decubitus ulcers, venous ulcers, ischemic ulcers, cancerous ulcers, aphthous ulcers, sublingual ulcers and atomic ulcers. When the water soluble beta-glucan is utilized in treating ulcers, it may be present in a composition in amounts ranging from about 0.1 to about 25%, based on the weight of the ingredients in the composition as recited above.

The soluble beta-glucan can be applied directly to the affected area as a mixture, or rinse, or gel followed by e.g. a dressing or a gauze pad when appropriate, or used in combination with pharmaceutical appliances like bandages, dressings, artificial skins, liposome or micelle formulations, microcapsules, aqueous vehicles for soaking gauze dressings, and the like, and mixtures thereof. Furthermore, the soluble beta-glucan can be applied by such as creams, gels, formulations, foams, ointments and sprays, salves, and films, which are intended to be applied to the affected area.

Typical examples of suitable mild, i.e. especially skin compatible surfactants, are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefine sulphonates, ethercarboxylic acids, alkyl oligoglucosides, fatty acid glucamides, alkylamido betaines and/or protein fatty acid condensates, the last mentioned preferably based on wheat proteins.

As oil bodies use can be made of, for example, Guerbet alcohols based on fatty alcohols with 6 to 18, preferably 8 to 10 carbon atoms, esters of linear $C_6$-$C_{22}$ fatty acids with linear $C_6$-$C_{22}$ fatty alcohols, esters of branched $C_6$-$C_{13}$ carboxylic acids with linear $C_6$-$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isosteayl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In addition esters of linear $C_6$-$C_{22}$ fatty acids with branched alcohols, especially 2-ethylhexanol, esters of hydroxycarboxylic acids with linear or branched $C_6$-$C_{22}$ fatty alcohols, especially dioctyl malate, esters of linear and/or branched fatty acids with polyvalent alcohols (such as e.g. propylene glycol, dimeric diol or trimeric triol) and/or Guerbet alcohols, triglycerides based on $C_6$-$C_{10}$ fatty acids, liquid mixtures of mono-/di-/triglycerides based on $C_6$-$C_{18}$ fatty acids, esters of $C_6$-$C_{22}$ fatty alcohols and/or Guerbet alcohols with aromatic carboxylic acids, especially benzoic acid, esters of $C_2$-$C_{12}$ dicarboxylic acids with linear or branched alcohols with 1 to 22 carbon atoms or polyols with 2 to 10 carbon atoms and 2 to 6 hydroxyl groups, plant oils, branched primary alcohols, substituted cyclohexanes, linear and branched $C_6$-$C_{22}$ fatty alcohol carbonates, Guerbet carbonates, esters of benzoic acid with linear and/or branched $C_6$-$C_{22}$ alcohols (e.g. Finsolv® TN), linear or branched, symmetrical or unsymmetrical dialkyl ethers with 6 to 22 carbon atoms in each alkyl group, ring opening products of epoxydated fatty acid esters with polyols, silicone oils and/or aliphatic or naphthenic hydrocarbons, such as e.g. squalan, squalen or dialkyl cyclohexanes, can be used As emulsifiers, for example, nonionic surfactants from at least one of the following groups may be used:

(1) Addition products of 2 to 30 moles ethylene oxide and/or 0 to 5 moles propylene oxide on linear fatty alcohols with 8 to 22 C atoms, on fatty acids with 12 to 22 C atoms and on alkyl phenols with 8 to 15 C atoms in the alkyl group;
(2) $C_{12/18}$ fatty acid mono- and -diesters of addition products of 1 to 30 moles ethylene oxide and glycerol;
(3) glycerol mono- and diesters and sorbitan mono- and diesters of saturated and unsaturated fatty acids with 6 to 22 carbon atoms and their ethylene oxide addition products;
(4) alkyl mono- and oligoglycosides with 8 to 22 carbon atoms in the alkyl group and their ethoxylated analogues;
(5) addition products of 15 to 60 moles ethylene oxide on ricinus oil and/or hardened ricinus oil;
(6) polyol and especially polyglycerol esters, such as e.g. polyglycerol polyricinoleate, polyglycerol poly-12-hydroxystearate or polyglycerol dimerate isostearate, and also mixtures of compounds from more of these classes of substances;
(7) addition products of 2 to 15 moles ethylene oxide on ricinus oil and/or hardened ricinus oil;
(8) partial esters based on linear, branched, unsaturated or saturated $C_{6/22}$ fatty acids, ricinolic acid and 12-hydroxy stearic acid and glycerol, polyglycerol, pentaerythrite, dipentaerythrite, sugar alcohols (e.g. sorbitol), alkyl glucosides (e.g. methyl glucoside, butyl glucoside, lauryl glucoside) as well as polyglucosides (e.g. cellulose);
(9) mono-, di- and trialkylphosphates as well as mono-, di- and/or tri-PEG alkylphosphates and their salts;
(10) wool wax alcohols;
(11) polysiloxane/polyalkyl/polyether copolymers or corresponding derivatives;
(12) mixed esters of pentaerythrite, fatty acids, citric acid and fatty alcohol according to DE 1165574 PS and/or mixed esters of fatty acids with 6 to 22 carbon atoms, methyl glucose and polyols, preferably glycerol or polyglycerol,
(13) polyalkylene glycols, as well as
(14) glycerol carbonate.

The addition products of ethylene oxide and/or of propylene oxide on fatty alcohols, fatty acids, alkyl phenols, glycerol mono- and diesters as well as sorbitan mono- and -diesters of fatty acids or on ricinus oil are known products which are commercially available. They are mixtures of homologous substances, with average degree of alkoxylation corresponding to the ratio of the amounts of the substances ethylene oxide and/or propylen oxide and substrate, with which the addition reaction is carried out. $C_{12/18}$ fatty acid mono- and -diesters of addition products of ethylene oxide on glycerol are known from DE 2024051 PS as revertive fatting agents for cosmetic preparations.

$C_{8/18}$ alkyl mono- and oligoglycosides, their manufacture and their use is known from prior art. Their preparation can especially be carried out by reaction of glucose or oligosaccharides with primary alcohols having 8 to 18 C atoms. With regard to the glycoside residue both monoglycosides, where a cyclic sugar group is glycosidic bond to the fatty alcohol, and oligomeric glycosides with a degree of oligomerisation until preferably about 8, are suitable. The degree of oligomerization is then a statistical mean value, based on a distribution of homologues which is usual for such products of technical quality.

Zwitterionic surfactants can also be used as emulsifiers. The term zwitterionic surfactants is intended to mean such surface active compounds which in their molecule have at least a quatenary ammonium group and at least one carboxylate and one sulphonate group. Especially suitable zwitterionic surfactants are the so-called betaines such as the N-alkyl-N,N-dimethyl ammonium glycinates, for example the coco alkyldimethyl ammonium glycinate, N-acylaminopropyl-N,N-dimethyl ammonium glycinate, for example the coco acylaminopropyl dimethyl ammonium glycinate, and 2-alkyl-3-carboxylmethyl-hydroxyethyl imidazoline with in each case 8 to 18 C atoms in the alkyl or acyl-groups, as well as the coco acylaminoethyl hydroxyethylcarboxymethyl glycinate. Especially preferred is that under the CTFA term cocamidopropyl betaine known fatty acid amide derivative. Also suitable emulsifiers are ampholytic surfactants. Ampholytic surfactants are such surface active compounds which in addition to a $C_{8/18}$ alkyl or acyl group in the molecule at least contain a free amino group and at least one —COOH or —SO$_3$H group and which can form inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkylamidopropyl glycines, N-alkyltaurines, N-alkylsarcosines, 2-alkylaminopropionic acids and alkylamino acetic acids with in each case about 8 to 18 C atoms in the alkyl group. Especially preferable ampholytic surfactants are the N-coco alkylamino propionate, the coco acylamino ethylaminopropionate and the $C_{12/18}$ acylsarcosine. In addition to the ampholytic, also quaternary emulsifiers can be used, of which ester salts of the type of esterquats, preferably methylquaternised di-fatty acid triethanolamine ester salts, are especially preferable.

As hyperfatting agents substances such as for example lanolin and lecithin as well as polyethoxylated or acylated lanolin and lecithin derivatives, polyol fatty acid esters, monoglycerides and fatty acid alkanolamides can be used, whereby the last mentioned at the same time act as foam stabilisers.

As exemplary pearl gloss waxes the following should be mentioned: Alkylene glycolester, especially ethyleneglycol distearate; fatty acid alkanolamides, especially coco fatty acid diethanolamide; partial glycerides, especially stearic acid monoglyceride; esters of polyvalent, possibly hydroxysubstituted carboxylic acids with fatty alcohols with 6 to 22 carbon atoms, especially long chain esters of tartaric acid; fat substances, such as for example fatty alcohols, fatty ketones, fatty aldehydes, fatty ethers and fatty carbonates, wherein the sum of carbon atoms is at least 24, especially lauron and distearyl ethers; fatty acids such as stearic acid, hydroxystearic acid or behenic acid, ring opening products of olefine epoxides with 12 to 22 carbon atoms with fatty alcohols with 12 to 22 carbon atoms and/or polyols with 2 to 15 carbon atoms and 2 to 10 hydroxyl groups as well as their mixtures.

As consistency givers preferably use is made of fatty alcohols or hydroxy fatty alcohols with 12 to 22 and preferably 16 to 18 carbon atoms and additionally partial glycerides, fatty acids or hydroxy fatty acids. A combination of these substances with alkyl oligoglucosides and/or fatty acid-N-methyl glucamides with the same chain length and/or polyglycerol-poly-12-hydroxy stearates.

Suitable thickening agents are for example types of aerosil (hydrophilic silicic acids), polysaccharides, especially xanthan gum, guar-guar, agar-agar, alginates and tyloses, carboxymethyl celluloses and hydroxyethyl celluloses, as well as higher molecular polyethylenglycol mono- and diesters of fatty acids, polyacrylates, (e.g. Carbopols® from Goodrich or Synthalenes® from Sigma), polyacrylamides, polyvinyl alcohol and polyvinyl pyrrolidone, surfactants such as for example ethoxylated fatty acid glycerides, ester of fatty acids with polyols such as for example pentaerythrite or trimethylolpropane, fatty alcohol ethoxytates with narrow distribution of homologous or alkyl oligoglucosides as well as electrolytes such as sodium chloride and ammonium chloride.

Suitable cationic polymers are for example cationic cellulose derivatives, such as e.g. a quaternized hydroxyethyl cellulose, which is available under the name of Polymer JR 400® from Amerchol, cationic starch, copolymers of diallyl ammonium salts and acrylamides, quaternized vinylpyrrolidone/vinylimidazol polymers, such as e.g. Luviquat® (BASF), condensation products of polyglycols and amines, quaternized collagen polypeptides, such as for example lauryl dimonium hydroxypropyl hydrolyzed collagen (Lamequat®L/Grünau), quaternized wheat polypeptides, polyethyleneimine, cationic silicone polymers, such as e.g. amidomethicones, copolymers of adipic acid and dimethylamino hydroxypropyl diethylenetriamine (Cartaretine®/Sandoz), copolymers of acrylic acid with dimethyl diallylammonium chloride (Merquat® 550/Chemviron), polyamino polyamides, such as e.g. described in FR 2252840 A, as well as their cross-linked water soluble polymers, cationic chitin derivatives such as for example quaternized chitosane, possibly micro crystalline distributed, condensation products of dihalogen alkyls, such as e.g. dibromobutane with bisdialkylamines, such as e.g. bis-dimethylamino-1,3-propane, cationic guar-gum, such as e.g. Jaguar® CBS, Jaguar® C-17, Jaguar® C-16 from Celanese, quaternised ammonium salt polymers, such as e.g. Mirapol® A-15, Mirapol® AD-1, Mirapol® AZ-1 from Miranol.

As exemplary anionic, zwitterionic, amphoteric and nonionic polymers the following can be used: Vinyl acetate/crotonic acid copolymers, vinyl pyrrolidone/vinyl acrylate copolymers, vinyl acetate/butyl maleate/isobornyl acrylate copolymers, methyl vinylether/maleic acid anhydride copolymers and their esters, non-cross-linked and with polyols cross-linked polyacrylic acids, acrylamido propyltrimethyl ammonium chloride/acrylate copolymers, octylacrylamide/methyl methacrylate/tert.-butylaminoethyl methacrylate/2-hydroxypropyl methacrylate copolymers, polyvinylpyrrolidone, vinylpyrrolidone/vinylacetate copolymers, vinylpyrrolidon/dimethylamino ethylmethacrylate/vinyl caprolactam terpolymers as well as possibly derivatized cellulose ethers and silicones.

Suitable silicon compounds are for example dimethyl polysiloxane, methylphenyl polysiloxane, cyclic silicones as well as amino, fatty acid, alcohol, polyether, epoxy, fluorine, glycoside and/or alkyl modified silicon compounds, which at room temperature can be in the liquid as well as in the resin state. Further suitable are simethicones, which are mixtures of dimethicones with an average chain length of 200 to 300 dimethyl siloxane units and hydrogenated silicates. A detailed survey of suitable volatile silicones can also be found in Todd et al., *Cosm. Toil.* 91, 27 (1976).

Typical exemplary fats are glycerides, and as waxes natural waxes among others, can be used, such as e.g. candelilla wax, carnauba wax, Japan wax, espartogras wax, cork wax, guaruma wax, rice seed oil wax, sugar cane wax, ouricury wax, montan wax, beeswax, schellack wax, spermaceti, lanolin (wool wax), burzel fat, ceresin, ozokerit (terrestrial wax), petrolatum, paraffin waxes, micro waxes; chemically modified waxes (hard waxes), such as e.g. montanester waxes, sasot waxes, hydrogenated yoyoba waxes as well as synthetic waxes, such as e.g. polyalkylene waxes and polyethylene glycol waxes.

As stabilizers metal salts of fatty acids, such as e.g. magnesium, aluminium and/or zinc stearate or ricinoleate can be used.

As biogenic active substances should be understood for example tocopherol, tocopherol acetate, tocopherol palmitate, ascorbic acid, desoxy ribonucleic acid, retinol, bisabolol, allantoin, phytantriol, panthenol, AHA acids, aminoacids, ceramides, pseudoceramides, essential oils, extracts of plants and vitamin complexes.

As deo active agents e.g. antiperspirants such as aluminium chlorohydrate come into question. This agent is in the form of colourless, hygroscopic crystals, which easily melt in air, and is obtained through evaporation of solutions of aluminium chloride in water. Aluminium chlorohydrate is used for manufacturing of perspiration inhibiting and deodorising preparations and has probably its effect through the partial closure of the perspiratory gland by means of precipitation of proteins and/or polysaccharides (see *J. Soc. Cosm. Chem.* 24, 281 (1973)). Under the trade name Locron® of Hoechst AG, Frankfurt/FRG, an aluminium chlorohydrate is for example on the market, which corresponds to the formula $[Al_2(OH)_5Cl].2.5H_2O$, and use of this is especially preferred (see *J. Pharm. Pharmacol.* 26, 531 (1975)]. In addition to the chlorohydrates also aluminium hydroxylactates as well as acid aluminium/zirconium salts can be used. As further deo active agents esterase inhibitors can be added. These are preferably trialkyl citrates such as trihethyl citrate, tripropyl citrate, triisopropyl citrate, tributyl citrate and especially triethyl citrate (Hydagen® CAT, Henkel KGaA, Düsseldorf/FRG). The substances inhibit the enzyme activity and thereby reduce the formation of odours. Probably the free acid is thereby set free through the cleavage of the citric acid ester, and this acid lowers the pH value of the skin so much that the enzymes thereby are inhibited. Further substances which can be used as estersase inhibitors are sterol sulphates or phosphates, such as for example lanosterol, cholesterol, campesterol, stigmasterol and sitosterol sulphate or phosphate, Dicarboxylic acids and their esters, such as for example glutaric acid, glutaric acid monoethylester, glutaric acid diethylester, adipic acid, adipic acid monoethylester, adipic acid diethylester, malonic acid and malonic acid diethylester, hydroxycarboxylic acids and their esters, such as for example citric acid, malic acid, tartaric acid or tartaric acid diethylester. Antibacterial active substances, which influence the germ flora and kill sweat destroying bacteria or inhibit their growth, can also be contained in the pin preparations. Examples of this are chitosan, phenoxyethanol and chlorohexidin gluconate. Also 5-chloro-2-(2,4-dichlorophen-oxy)-phenol has shown to have an especially good effect, and this product is marketed under the trade name Irgasan® by Ciba-Geigy, Basel/CH.

As anti-dandruff agents, climbazol, octopirox and zinc pyrethion can be used. Useable film formation agents are for example chitosan, microcrystalline chitosan, quaternary chitosan, polyvinylpyrrolidon, vinylpyrrolidon/vinylacetate copolymers, polymers of the acrylic acids, quaternary derivatives of cellulose, collagen, hyaluronic acid or its salts and similar compounds. As swelling agents for aqueous phases, montmorillonite, clay mineral substances, pemulen, as well as alkylmodified Carbopol types (Goodrich) can be used. Further suitable polymers or swelling agents can be found in the survey of R. Lochhead in *Cosm. Toil.* 108, 95 (1993).

UV light protection factors are e.g organic substances (light protection filters) which by room temperature are in liquid or crystalline form, and which are capable of absorbing ultraviolet radiation and to set free the received energy in the form of radiation with long wavelength, e.g. in the form of heat. UVB filters can be soluble in oils or in water. As oil soluble substances the following are mentioned as examples:

3-benzyliden camphor, respectively 3-benzylidene norcamphor and the derivatives thereof, e.g. 3-(4-methylbenzylidene) camphor as described in EP-B1 0693471;

4-aminobenzoic acid derivatives, preferably 4-(dimethylamino) benzoic acid 2-ethylhexylester, 4-(dimethylamino) benzoic acid 2-octylester and 4-(dimethylamino) benzoic acid amylester;

esters of cinnamonic acid, preferably 4-methoxy cinnamonic acid 2-ethylhexylester, 4-methoxy cinnamonic acid propylester, 4-methoxy cinnamonic acid isoamylester, 2-cyano-3,3-phenyl cinnamonic acid 2-ethyhexylester (octocrylene);

esters of salicylic acid, preferably salicylic acid 2-ethylhexylester, salicylic acid 4-isopropyl benzylester, salicylic acid homomenthylester;

derivatives of benzophenone, preferably 2-hydroxy-4-methoxy benzophenone, 2-hydroxy-4-methoxy-4'-methyl benzophenone, 2,2'-dihydroxy-4-methoxy benzophenone;

esters of benzalmalonic acid, preferably 4-methoxy benzmalonic acid 2-ethylhexyl ester, triazine derivatives, such as e.g. 2,4,6-trianilino-(p-carbo-2'-ethyl-1'-hexyloxy)-1,3,5-triazine and octyltriazone, as described in EP A1 0818450;

propane-1,3-diones, such as e.g. 1-(4-tert.-butylphenyl)-3-(4'-methoxy-phenyl)-propane-1,3-dion;

ketotricyclo(5,2,1,0)-decane derivatives, as described in EP-B1 06945521. As water soluble substances the following can be mentioned:

2-Phenylbenzimidazol-5-sulphonic acid and the alkali, alkaline earth, ammonium, alkylammonium, alkanolammonium and glucammonium salts;

sulphonic acid derivatives of benzophenones, preferably 2-hydroxy-4-methoxybenzophenon-5-sulphonic acid and their salts;

sulphonic acid derivatives of 3-benzylidencamphen, such as e.g. 4-(2-oxo-3-bornylidenmethyl)-benzene sulphonic acid and 2-methyl-5-(2-oxo-bornyliden) sulphonic acid and their salts.

As typical UV-A filters especially derivatives of benzoyl methane comes in question, such as e.g. 1-(4'-tert.-butylphenyl)-3-(4'-methoxyphenyl)propane-1,3-dion, 4-tert.butyl-4'-methoxydibenzoyl-methane (Parsol 1789), or 1-phenyl-3-(4'-isopropylphenyl-propane-1,3-dion. The UV-A and UV-B filters can of course also be used in mixtures. In this case combinations of octocrylene or camphor derivatives with butyl methoxydibenzoylmethane are especially photosensitive.

In addition to the mentioned soluble substances also insoluble light protection pigments can be used for this purpose, i.e. fine disperse metal oxides or salts. Examples of suitable metal oxides are especially zinc oxide and titanium dioxide and in addition other oxides of iron, zirconium, silicon, manganese, aluminium and cerium, as well as their mixtures. As salts silicates (TALL), barium sulphate or zinc stearate can be used. The oxides and salts are used in the form of the pigments for skin caring and skin protecting emulsions and decorative cosmetics. The particles should have an average diameter of less than 100 nm, preferably between 5 and 50 nm and especially between 15 and 30 nm. They can have a spherical shape, but particles can also be used which have an ellipsoidal form or else have a shape which differs from the spherical shape. In sun protecting agents preferably so-called micro or nano pigments are used. Preferably micronized zinc oxide is used. Further suitable UV light protection factors can be found in the survey by P. Finkel in *SÖFW-Journal* 12, 543 (1996). Likewise suitable are herbal extracts with UV absorbing or antioxidative properties.

In addition to the primary light protection substances also secondary light protection substances of the antioxidant type find use, which interrupt the photochemichal reaction chain, which is initiated when UV radiation penetrates the skin. Typical examples of such are amino acids (e.g. glycin, histidin, tyrosin, tryptophan) and their derivatives, imidazoles (e.g. urocaninic acid) and their derivatives, peptides such as D,L-carnosine, D-carnosine, L-carnosine and their derivatives (e.g. anserine), carotinoides, carotine (e.g. α-carotin, β-carotin, lycopin) and their derivatives, chlorogenic acid and its derivatives, liponic acid and its derivatives (e.g. dihydroliponic acid), aurothioglucose, propylthiouracil and other thiols (e.g. thioredoxin, glutathion, cystein, cystin, cystamine and their glycosyl, n-acetyl, methyl, ethyl, propyl, amyl, butyl and lauryl, palmitoyl, oleyl, γ-linoleyl, cholesteryl and glyceryl esters) as well as their salts, dilauryl thiodipropionate, distearyl thiodipropionate, thiodipropionic acid and their derivatives (esters, ethers, peptides, lipides, nucleotides, nucleosides and salts) as well as sulfoximine compounds (e.g. buthionin sulfoximines, homocystein sulfoximines, butionin sulfones, penta-, hexa-, hepta-thionin sufoximine) in very small compatible doses (e.g. pmol to μmol/kg), further (metal) chelating agents (e.g. α-hydroxy fatty acids, palmitic acid, phytinic acid, lactoferrine), α-hydroxy acids (e.g. citric acid, lactic acid, malic acid), humin acid, gallic acid, gallic extracts, bilirubin, bifiverdin, EDTA, EGTA and their derivatives, unsaturated fatty acids and their derivatives (e.g. γ-linolenic acid, linolic acid, oleic acid), folic acid and their derivatives, ubichinon and ubichinol and their derivatives, vitamin C and derivatives (e.g. ascorbyl palmitate, Mg-ascorbyl phosphate, ascorbyl acetate), tocopheroles and derivatives (e.g. vitamin E acetate), vitamin A and derivatives (vitamin A patmitate) as well as koniferyl benzoate of benzoe resin, rutinic acid and their derivatives, α-glycosylrutin, ferula acid, furfuryliden glucitol, carnosine, butylhydroxy toluene, butylhydroxy anisol, nordihydro guajak resin acid, nordihydro guajaret acid, trihydroxy butyrophenon, uric acid and their derivatives, mannose and its derivatives, super oxide dismutase, zinc and its derivatives (e.g. ZnO, ZnSO$_4$), selen and its derivatives (e.g. selen-methionin), stilbenes and their derivatives (e.g. stilben oxide, trans-stilben oxide) and the derivatives suitable according to the invention (salts, esters, ethers, sugars, nucleotides, nucleosides, peptides and lipids) of these mentioned active substances.

For improvement of the flow properties further hydrotropes, such as for example ethanol, isopropyl alcohol, or polyols can be used. Polyols which in this case can be used preferably have 2 to 15 carbon atoms and at least two hydroxyl groups. The polyols can further contain additional functional groups, especially amino groups, or be modified with nitrogen. Typical examples are:

Glycerol;

alkylen glycols, such as for example ethylene glycol, diethylene glycol, propylene glycol, butylene glycol, hexylene glycol as well as polyethylen glycols with an average molecular weight from 100 to 1 000 Daltons;

oligoglycerol mixtures of technical quality with a self-condensation degree of 1.5 to 10, such as e.g. technical quality diglycerol mixtures with a diglycerol content of 40 to 50% by weight;

methyol compounds, such as especially trimethylol ethane, trimethylol propane, trimethylol butane, pentaerythrite and dipentaerythrite;

low alkyl glucosides, especially such with 1 to 8 carbons in the alkyl residue, such as for example methyl and butyl glucoside;

sugar alcohols with 5 to 12 carbon atoms, such as for example sorbitol or mannit;

sugars with 5 to 12 carbon atoms, such as for example glucose or saccharose;

aminosugars, such as for example glucamine;

dialcoholamines, such as diethanolamine or 2-amino-1,3-propanediol.

As preservatives for example phenoxyethanol, formaldehyde solution, parabene, pentanediol or sorbic acid as well as those mentioned in enclosure 6, parts A and B of the cosmetic regulation, are further classes of substances. As insect repellents N,N-diethyl-m-toluamide, 1,2-pentanediol or insect repellent 3535 come into question, as self tanning agent dihydroxyaceton is suited.

As perfume oils mixtures of natural and synthetic scent substances should be mentioned. Natural scent substances are extracts of flowers (lilies, lavendel, roses, jasmin, neroli, ylang-ylang), stems and blades (geranium, patchouli, petitgrain), fruits (anis, coriander, caraway, juniper), fruit shells (bergamot, lemon, orange), roots (macis, angelica, celery, kardamon, costus, iris, calmus), wood (stone pine, sandel, guajac, cedar, rosewood), herbs and grass (tarragon, lemongrass, sage, thyme), needles and twigs (spruce, fir, pine, traipsed), resins and balsams (galbanum, elemi, benzoe, myrrh, olibanum, opoponax). Raw materials from animals are also possible, such as for example zibet and castoreum. Typical synthetic odour compounds are products from types of esters, ethers, aldehydes, ketones, alcohols and hydrocarbons. Odour compounds from types of esters are e.g. benzyl acetate, phenoxyethyl isobutyrate, p-tert.-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. Benzylethyl ether belongs for example to the ethers, to the aldehydes e.g. the linear alkanales with 8 to 18 carbon atoms, citral, citronellal, citronellyl oxyacetaldehyde, cyclamen aldehyde, hydroxy citronellal, lilial and bourgeonal, to the ketones e.g. the ionones, α-isomethyl ionon and methylcedryl ketone, to the alcohols anethol, citronellol, eugenol, isoeugenol, geraniol, linalool, phenylethyl alcohol and terpineol; to the hydrocarbons mainly the terpenes and balsams belong. However, mixtures of different odour substances are preferred, which together give a pleasant smell. Also etheral oils with low volatility, which often are used as aroma components, are suited as perfume oils, e.g. sage oil, chamomile oil, carnation oil, melissa oil, mint oil, cinnamon leaf oil, limeflower oil, juniper berry oil, vetiver oil, oliban oil, galbanum oil, labolanum oil and lavandin oil. Preferably used are bergamot oil, dihydromyrcenol, lilial, lyral, citronellol, phenylethyl alcohol, α-hexylcinnamon aldehyde, geraniol, benzylaceton, cyclamen aldehyde, linalool, boisambrene forte, ambroxane, indol, hedione, sandelice, lemon oil, mandarin oil, orangenoil, allylamyl glycolate, cyclovertal, lavandine oil, muskateller sage oil, β-damascone, geranium oil bourbon, cyclohexyl salicylate, vertofix coeur, iso-E-super, fixolide NP, evemyl, iraidein gamma, phenylacetic acid, geranyl acetate, benzyl acetate, rose oxide, romillate, irotyl and floramate, alone or in mixtures.

As colouring agents such substances which are suited and approved for cosmetic purposes can be used, such as for example those mentioned in the publication *"Kosmetische Färbemittel" (cosmetic dyes) of the "Farbstoffkommission der Deutschen Forschungsgemeinschaft"*, published by Verlag Chemie, Weinheim, 1984, p. 81-106. These dyes are generally used in concentrations from 0.001 to 0.1% by weight, based on the whole mixture.

Typical examples of germ inhibiting substances are preservatives with specific effects against gram-positive bacteria, such as 2,4,4'-trichloro-2'-hydroxy diphenylether, chlorohexidin (1,6-di-(4-chlorophenyl-biguanido-hexan) or TCC (3,4,4'-trichlorocarbanilide). Many scent substances and etheral oils also have antimicrobial properties. Typical examples are the active agents eugenol, menthol and thymol in carnation, mint and thyme oil. An interesting natural deo substance is the terpene alcohol farnesol (3,7,11-trimethyl-2,6,10-dodecatrien-1-ol), which is present in lime flower oil and has a smell of lilies of the valley. Also, glycerol monolaurate have been used as bacteriostaticum. Normally the content of the further germ inhibiting agent is about 0.1 to 2% by weight—based on the solids content of the preparations.

The cumulative contents of the auxiliary and additional agents can be 1 to 50, preferably 5 to 40% by weight, based on the agents. The manufacture of the agents can take place by common cold or hot processes; preferably the work is carried out according to the phase inversion temperature method.

EXAMPLES

By way of example, the following experiments demonstrate that the β-glucans of the invention work as active agents for combating the formation of wrinkles in the skin as well as epithelial tissue diseases, e.g. ulcers. The following examples are meant to illustrate the invention. They are not intended to limit the scope of the invention in any manner or to any degree.

Example I

A panel consisting of 15 female probands aged between 35 and 50 years were during a time period of 28 days daily exposed to a daily exposition of different glucans. For this purpose O/W skin cremes with the composition stated in table 1 was made by mixing of the phases I and II at 95° C.

TABLE 1

Composition of O/W Skin Cremes

| Composition | Phase I | Phase II |
|---|---|---|
| Cetylstearyl alcohol | 8.0 | — |
| Ceteareth-12 | 1.5 | — |
| Ceteareth-20 | 1.5 | — |
| Cetearyl isononanoate | 15.0 | |
| Paraffin oil, viscous | 5.0 | |
| Baysilon oil M 300 | 5.0 | |
| Glucan | | 20.0 |
| Glycerol | | 6.0 |
| Water | — | 38.0 |
| Sum | 36.0 | 64.0 |

The probands used the skin cremes daily before going to bed. With intervals of 7 days the number, depth and length of the skin wrinkles were determined for each of the participants by means of profilometry of a selected part of the skin, i.e. a vertical stripe of 2 cm width and 5 cm length, having an upper left and right boundary. which occurs if from the nose root a horizontal line is drawn, from this and against the right eye 2, respectively 4 cm, are cleared away and both resulting points in each case are elongated in an angle of 270° in each case 2 cm. The dimensionless product of depth, number and length of the skin wrinkles on the day before the beginning of the exposure was set as standard (=100%), and all the following measurements were related to this. At the same time the skin roughness of the pro-bands was evaluated on a scale from 0="unchanged" to 3="strongly improved". The results are summarized in table 2. Example 1 is according to the invention, the examples V1 to V7 are for comparison. It can be seen that the water soluble β-(1,3) glucans of the invention, which have no (1,6) linkages, exhibit a better effect than known glucans according to the state of the art.

TABLE 2

Skin aging and Skin Roughness

| | | Skin aging after [d] in [%] | | | | | Skin roughness after [d] | | | |
|---|---|---|---|---|---|---|---|---|---|---|---|
| Ex. | Glucan | 0 | 7 | 14 | 21 | 28 | 0 | 7 | 14 | 21 | 28 |
| 1 | β-1,3 Glucan | 100 | 96 | 91 | 85 | 79 | 0 | 1 | 2 | 3 | 3 |
| V1 | Schizophyllan[1)] | 100 | 98 | 95 | 90 | 86 | 0 | 0 | 1 | 2 | 3 |
| V2 | Krestin[3)] | 100 | 99 | 96 | 92 | 88 | 0 | 0 | 0 | 1 | 2 |
| V3 | Sclereoglucan[4)] | 100 | 100 | 99 | 96 | 88 | 0 | 0 | 0 | 1 | 2 |
| V4 | CM-Glucan[5)] | 100 | 100 | 99 | 96 | 95 | 0 | 0 | 0 | 1 | 1 |
| V5 | Mannozym[6)] | 100 | 100 | 100 | 99 | 98. | 0 | 0 | 0 | 1 | 1 |
| V6 | Lichenin[7)] | 100 | 100 | 100 | 100 | 98 | 0 | 0 | 0 | 0 | 1 |
| V7 | Isoiichenin[8)] | 100 | 100 | 100 | 100 | 98 | 0 | 0 | 0 | 0 | 1 |

Legend:
[1)] SBG, Biotec Pharmacon ASA, Tromsø
[2)] β-(1,3)-/β-(1,6) Glucan, extact from *Schizophyllum Commune*

Legend:
1) SBG, Biotec Pharmacon ASA, Tromsø
2) β-(1,3)-/β-(1,6) Glucan, extract from *Schizophyllum Commune*
3) β-(1,3)-/β-(1,4)-β-(1,6) Glucan-protein (30%) complex, extract from *Conolossus versicolor*
4) β-(1,3)/β-(1,6) Glucane, Extract from *Sclereoticum glucanium*
5) Carboxymethylated β-(1,3) glucan, extract from *Saccharomyces cervisiae*
6) α-Mannene with branches, extract from *Saccharomyces cervisiae*
7) β-(1,3)/β-(1,4) Glucan+α-(1,3)/α-(1,4) glucan mixture, extract from *Cetraria islandica* (extract of lichen)

Example II

A limited pilot clinical study examining the ability of the above described soluble beta-1,3/1,6-glucan to facilitate healing of diabetic ulcers was initiated. Fifteen patients with type 1 (1 patient) or type 2 (14 patients) diabetes were included (for inclusion and exclusion criteria, see Table 3). The single patient with type 2 diabetes was placed in the control group. All patients had clinically typical "neuropathic" ulcers of the lower extremities (stage II and III WHO criteria). SBG refers to the soluble beta glucan of this invention.

TABLE 3

Pilot study with topical SBG treatment of chronic diabetic ulcers

Inclusion criteria:

Type 1 or type 2 diabetes mellitus, complicated by chronic ulcers of the lower extremities (neuropathic type, 1-40 $cm^2$ after initial debridement; infection and cellulites controlled before randomisation)
Adequate arterial circulation (normal malleolus-brachial indices as determined by Doppler techniques)
Signed informed consent Exclusion criteria:

Osteomyelitis of affected area
Ulcer after debridement <1 $cm^2$ or >40 $cm^2$ or sum of all ulcers >100 $cm^2$
Patients with ulcers of other than diabetic etiology
Gangrene
Concomitant disease requiring radiotherapy, chemotherapy, immunosuppresive medications, corticosteroids, connective tissue disorder, cancer
Pregnant or lactating women Six patients received conventional therapy: diabetes control (systemic insulin, peroral sulfonyl urea), off-loading of pressure from the affected area; debridement and local application of antibacterial levamicol (0.75%). These six patients constituted the control group. Nine patients received similar diabetic control and debridement as the control group, but topical application of a 2% solution of soluble beta-1,3/1,6-glucan instead of levamicol (for details of treatment, see Table 4).

TABLE 4

Pilot study with topical SBG treatment of chronic diabetic ulcers
Treatment

Treatment was given every second day in the out-patient setting
and every day for hospitalized patients as follows:
Surgical debridement, removal of necrotic and hyperkeratotic tissues
Ulcers were washed with 0.9% NaCl
Soluble beta-1,3/1,6-glucan as 2% solution (in aq.pur.) or Levamicol
(0.75% levamicatin in polyethyleneoxide) treatment:
Dose = ulcer volume. In case of deep ulcers, a "gauzeball"
was inserted.
Covering with gauze bandages, etc All patients that received beta-glucan treatment had complete healing of ulcers within 100 days and most ulcers healed by day 35 (see FIG. 1).

In contrast, only 2 (of 6 eligible) patients in the control group achieved complete closure of ulcers and these lesions were both small (<2 cm2). In one control case, beta-glucan treatment had to be introduced after 2 weeks for ethical reasons (see asterisk, FIG. 1).

Example III

Herein is described the healing of aphthous ulcers in a 62 year old male, with a history of suffering from recurrent aphthous ulcers on the mucosal epithelial layer in the oral cavity during several years with reappearance every 3-12 months lasting for several weeks. The ulcer manifested as 2-6 mm first red edged and subsequently as white edged craters particularly under the tongue, but also elsewhere in the oral cavity. The patient started using 10 mL of a 10 mg/mL SBG solution as an oral rinse every second day during outbreak of the ulcers, resulting in complete healing of the ulcers during the first week of treatment. The patient has for three years used SBG as weekly rinse, and has since the start of treatment not suffered from recurrence of aphthous ulcers.

What is claimed is:

1. A method of treating a subject suffering from an ulcer, said method comprising applying topically to the ulcer a preparation comprising a water-soluble branched $\beta$-(1,3)-glucan having $\beta$-(1,3)-linked chains, and having essentially no $\beta$-(1,6)-linked side-chains, wherein said glucan originates from the yeast family Saccharomyces and is obtainable by contacting glucans having $\beta$-(1,3) and $\beta$-(1,6) linkages with a $\beta$-(1,6) glucanase such that essentially all $\beta$-(1,6)-linked side-chains are cleaved; wherein said ulcer is selected from the group consisting of a diabetic ulcer, a plantar ulcer, a decubitus ulcer, a venous ulcer, an ischemic ulcer, a cancerous ulcer, an aphthous ulcer, a sublingual ulcer and an atonic ulcer.

2. The method according to claim 1, wherein the glucan is used in an amount of 0.1% to 25% by weight based on the preparation.

3. The method of claim 1, wherein the ulcer is chronic ulcer.

4. The method of claim 1, wherein said glucanase is obtained from *Trichoderma harzianum*.

5. The method of claim 1, wherein said glucan comprises no more than four consecutive $\beta$-(1,6)-linkages in the $\beta$-(1,6) side-chains.

6. A method of treating an ulcer comprising the steps of:
   a. isolating a branched $\beta$-(1,3) glucan with $\beta$-(1,6) linked side-chains from the yeast family Saccharomyces;
   b. cleaving off essentially all $\beta$-(1,6) linkages and obtaining a cleaved branched $\beta$-(1,3)-glucan having $\beta$-(1,3) linked side-chains attached by a $\beta$-(1,6) linkage and being essentially free of $\beta$-(1,6) linked side-chains;
   c. preparing a solubilized preparation containing therein the said cleaved glucan in amounts of 0.1% to 25% by weight; and
   d. applying topically said preparation to an ulcer;
   wherein said ulcer is selected from the group consisting of a diabetic ulcer, a plantar ulcer, a decubitus ulcer, a venous ulcer, an ischemic ulcer, a cancerous ulcer, an aphthous ulcer, a sublingual ulcer and an atonic ulcer.

7. The method of claim 6, wherein said cleaved branched $\beta$-(1,3)-glucan has no more than four consecutive $\beta$-(1,6)-linkages in the $\beta$-(1,6) side-chains.

8. The method of claim 6, wherein said ulcer is a chronic ulcer.

9. The method of claim 6, wherein said glucan is produced by reaction with a $\beta$-(1,6) glucanase.

10. The method of claim 9, wherein said glucanase is isolated from *Trichoderma harzianum*.

* * * * *